United States Patent
Barras et al.

(10) Patent No.: US 7,449,592 B2
(45) Date of Patent: Nov. 11, 2008

(54) PROCESS FOR THE PREPARATION OF METHYLALUMINIUM DICHLORIDE

(75) Inventors: Jean-Pierre Barras, Geneva (CH); Fridtjof Wai Schröder, Hettlingen (CH)

(73) Assignee: Givaudan SA, Vernier (CH)

( * ) Notice: Subject to any disclaimer, the term of this patent is extended or adjusted under 35 U.S.C. 154(b) by 350 days.

(21) Appl. No.: 10/568,831

(22) PCT Filed: Aug. 13, 2004

(86) PCT No.: PCT/CH2004/000505

§ 371 (c)(1),
(2), (4) Date: Feb. 17, 2006

(87) PCT Pub. No.: WO2005/016938

PCT Pub. Date: Feb. 24, 2005

(65) Prior Publication Data

US 2006/0264675 A1    Nov. 23, 2006

(30) Foreign Application Priority Data

Aug. 18, 2003  (GB) ................................. 0319277.0

(51) Int. Cl.
  *C07F 5/06* (2006.01)
  *C07C 45/61* (2006.01)
(52) U.S. Cl. ....................................... 556/186; 568/343
(58) Field of Classification Search ................. 556/186; 568/343
  See application file for complete search history.

(56) References Cited

U.S. PATENT DOCUMENTS 2,712,546 A   7/1955   Hunter et al.
2,848,472 A   8/1958   Cottle
5,707,961 A   1/1998   Bajgrowicz et al.

OTHER PUBLICATIONS

International Search Report dated Nov. 19, 2004 for application PCT/CH2004/000505.
Written Opinion of the International Searching Authority for application PCT/CH2004/000505.
*J. Am. Chem. Soc.* 73, 2854 (1951).
Grosse and Mativy in *J. Org. Chem.* 5, 106 (1940).
Houben-Weyl "Methoden der organischen Chemie" (Thieme Verlag, 1970), Bd 13/4, pp. 59-78).

*Primary Examiner*—Porfirio Nazario Gonzalez
(74) *Attorney, Agent, or Firm*—Norris McLaughlin & Marcus, PA

(57) ABSTRACT

A process of preparing methylaluminium dichloride by
  (i) reacting by heating a material of the formula $R_3Al_2X_3$, where R is $C_1$-$C_4$ alkyl and X is selected from bromine and iodine with an aluminium-containing material selected from metallic aluminium and a mixture of metallic aluminium and aluminium trichloride in an atmosphere of methyl chloride, with the proviso that when R is methyl and X is iodine, the aluminium-containing material is a mixture of aluminium and aluminium trichloride; and
  (ii) when the aluminium-containing material is metallic aluminium, adding aluminium trichloride to this reaction mixture and heating,
to give a crude reaction product; and
  (iii) if desired, obtaining methylaluminium dichloride from this crude reaction product.

The crude reaction product may be used directly in organic syntheses, such as the cyclisation of ψ-Georgywood to give β-Georgywood.

7 Claims, No Drawings

PROCESS FOR THE PREPARATION OF METHYLALUMINIUM DICHLORIDE

This invention relates to a method of preparing methylaluminium dichloride and to its use in the preparation of certain fragrant substances.

Methylaluminium dichloride (MADC) was characterised and procedures for its preparation were published some time ago (for example, *J. Org. Chem.* 5, 106 (1940)). Several later publications described its preparation (for example, *J. Am. Chem. Soc.* 73, 2854 (1951) and U.S. Pat. No. 2,712,546).

MADC is potentially useful as a Lewis acid in syntheses, but its use has been hindered by the fact that is is difficult to make consistently and inexpensively on an industrial scale (see, for example, Houben-Weyl "Methoden der organischen Chemie" (Thieme Verlag, 1970), Bd 13/4, pp. 59-78).

It has now been found that it is possible to prepare MADC by a cheap, efficient process that gives a good yield of the compound. It has the additional advantage that the unpurified compound as prepared can be used directly in the preparation of desirable organic compounds. The invention therefore provides a process for the preparation of MADC comprising the steps of (i) reacting by heating a material of the formula $R_3Al_2X_3$, where R is $C_1$-$C_4$ alkyl and X is selected from bromine and iodine, with an aluminium-containing material selected from metallic aluminium and a mixture of metallic aluminium and aluminium trichloride in an atmosphere of methyl chloride, with the proviso that, when R is methyl and X is iodine, the aluminium-containing material is a mixture of aluminium and aluminium trichloride; and (ii) when the aluminium-containing material is metallic aluminium, adding aluminium trichloride to this reaction mixture and heating, to give a crude reaction product; and (iii) if desired, obtaining methylaluminium dichloride from this crude reaction product.

The compound of formula $R_3Al_2X_3$ as hereinabove defined (hereinafter "the sesquihalide") may be any such material, but it is preferably selected from methylaluminium sesquiiodide (MASI) and ethylaluminium sesquibromide (EASB). The sesquihalide may be a pure material, but it is preferably the crude mixture of unreacted raw materials and product resulting from the preparation method described by Grosse and Mativy in *J. Org. Chem.* 5, 106 (1940), the details of which are incorporated herein by reference. This describes the MASI preparation, (in this case, the mixture is aluminium, unreacted methyl iodide and MASI), but EASB and the other sesquihalides may be prepared by an exactly analogous method.

This crude sesquihalide mixture is added directly to an aluminium-containing material. The aluminium-containing material is preferably metallic aluminium in particulate form, more preferably it is aluminium gritty. An example of a suitable material is Fluka™ 11008 in the Sigma-Aldrich Catalogue. The aluminium-containing material may also be a mixture of metallic aluminium and aluminium trichloride. When the sesquihalide is MASI, the aluminium-containing material must be such a mixture. The weight ratio of Al to $AlCl_3$ is preferably from 2:1 to 3:1.

The method comprises the following steps:

(i) the crude sesquihalide mixture is sprinkled over the aluminium-containing material in an atmosphere of methyl chloride at a pressure of 1 bar, and the mixture heated; and then (ii) when the aluminium-containing material is metallic aluminium, the aluminium chloride is added and the mixture is again heated.

Naturally, when the aluminium-containing compound is an aluminium/aluminium trichloride mixture, step (ii) above is unnecessary.

The following reaction conditions are typical and are given by way of guidance only—the skilled person will know what adjustments will be necessary in each case. Although they are described with reference to the preferred MASI and EASB, the same principles apply for the preparation of all sesquihalides.

The reaction conditions needed to start the reaction are slightly different, depending on whether MASI or EASB will be used. The starting temperature for MASI may be room temperature (20-25° C.), but slight heating may be needed in the case of EASB (about 45° C.). From this point on, the conditions are similar; the temperature is raised to about 115°-120° C. and maintained there for 4-6 h. At this point, the temperature is lowered to 60°-70° C., and non-polar solvent, typically toluene or cyclohexane, may be added, if need be.

The yield in both cases is typically at least 75% MADC, based on the weight of the aluminium-containing material.

The proportions of crude sesquihalide used are from 0.2-20%, preferably from 0.5-5% by weight of the aluminium-containing material. Without restricting the invention in any way, it is believed that the sesquihalide acts as an activator for the aluminium. It is preferred not to exceed 10% purely for cost reasons—more can be used, but it has no greater effect.

If desired, pure MADC may be produced from the resulting crude MADC by distillation. However, in another aspect of this invention, this crude MADC may be used in this form to promote a desirable organic reaction. Thus, the invention also provides a method of producing β-Georgywood, comprising the addition of pseudo-Georgywood (ψ-Georgywood) to the abovementioned crude MADC.

β-Georgywood (cis-2-acetyl-1,2,3,4,5,6,7,8-octahydro-1,2,8,8-tetramethylnaphthalene) is a fragrance ingredient having the formula I:

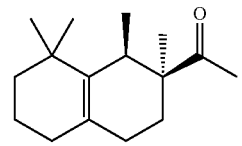

I

This fragrant material is described in U.S. Pat. No. 5,707,961, the details of which are incorporated herein by reference. It is known from this patent that Compound I may be prepared by the cyclisation of ψ-Georgywood (cis-1-[1,2-dimethyl-4(4-methyl-pent-3-enyl)-cyclohex-3-enyl]-ethanone—Formula II):

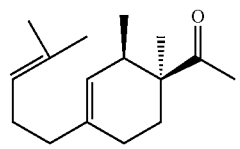

II

The method of preparing the compound of Formula I from that of Formula II is described in paragraph (d) of Example 1 of the abovementioned US patent. However, that preparation gives a mixture of Compound I and its structural isomer iso-Georgywood, shown in Formula III:

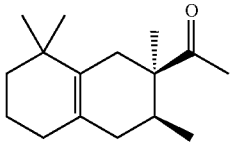

III

The compound of Formula I has particularly desirable olfactory properties. It is therefore desirable to increase the proportion of the compound of Formula I in the mixture. Achieving this using the technology of U.S. Pat. No. 5,707,961 is very difficult.

The process of preparation of β-Georgywood according to the present invention gives a number of distinct advantages:
1. The compound of Formula I is obtained in a yield of more than 80% and in a purity of higher than 90%. The compound of Formula III is present only in trace amounts (less than 1%).
2. The reaction can be carried out as a "one pot" reaction, that is, all the reactions from the initial MADC preparation to the final product reaction can be carried out in a single reaction vessel, without the need to isolate and purify intermediates.

Both of these are of considerable significance to the preparation of β-Georgywood on a commercial scale.

A further advantage of the method of this invention is that the compound of Formula I made by the abovementioned process can be easily decoloured, something that is difficult to achieve with products obtained from iodine-containing reagents. For example, a product obtained using MASI as starting material is easily decoloured by stirring or distilling over an acidic clay. In this regard, the product obtained by using EASB as starting material is even better, in that decolorisation is not necessary.

The process is carried out simply by adding Compound II to the crude MADC and heating for about 4 hours at about 60°-70° C.

The invention is further described with reference to the following non-limiting examples.

EXAMPLE 1

Preparation of Crude MASI, Crude MASC and MADC (Distilled)

Under nitrogen 18.2 g (0.13 mol) methyl iodide and 2 g (0.75 mol) aluminium gritty (Fluka™ 110008) are heated to reflux (45° C.) for 8-12 h. The resulting crude MASI reaction mixture can be stored under nitrogen for several weeks without loss of activity.

16.2 g (0.6 mol) aluminium gritty (Fluka 11008) is placed under 1 atm of methyl chloride (dried over a column filled with KOH) in a sulphonation flask equipped with a reflux condenser and a balloon fixed on the gas-outlet. 0.4 ml (ca. 5% w/w) of the above aluminium/methyl iodide/MASI mixture is sprinkled via syringe over the aluminium at 90° C. The reaction starts with a temperature rise to 120° C. and formation of liquid MASC. Under stirring, the reaction temperature is maintained at 120° C. for 4 h (by means of slight cooling and regulation of the methyl chloride flow) until the exothermy and the methyl chloride uptake (56 g, 1.1 mol) cease and the theoretical volume of 54 ml (d=1.15) liquid MASC is reached.

The methyl chloride atmosphere is replaced by nitrogen. The black liquid is cooled to 60° C., at which point 29 g (0.22 mol) aluminium chloride is added via a nitrogen-flushed proportioning screw. The black suspension is heated to 120° C. and maintained there for 30 min. Formation of MADC can be checked by briefly cooling to under 55° C., at which temperature the reaction mass solidifies. The proportioning screw is replaced by a distillation bridge and the MADC is distilled under 1 atm of nitrogen at bpt.=157° C. to give 69.3 g (75% based on aluminium and aluminium trichloride) of colourless MADC, which crystallizes at room temperature in long white needles.

Analytical Data:

MASI (crude): $^{27}$Al-NMR (neat): 71 ($W_{1/2}$=14800 Hz) ppm.

MASC (crude): $^{27}$Al-NMR (hexane): 177 ($W_{1/2}$=7600 Hz), 136 ($W_{1/2}$=6000 Hz) ppm.

MADC (dist): Fp=73° C., bp=157° C. $^{27}$Al-NMR (hexane): 136 ($W_{1/2}$=6000 Hz) ppm.

EXAMPLE 2

Cyclization of Pseudo-Georgywood (ψ-Georgywood) With Commercial MADC: (cis-2-acetyl-1,2,3,4,5,6,7,8-octahydro-1,2,8,8-tetramethylnaphthalene (β-Georgywood)

20 g (85 mmol) ψ-Georgywood dissolved in 100 g toluene is added under ice cooling to 157 g (0.21 mol) MADC (1 M in hexane, Aldrich™ 29680-5). The mixture is heated to 70° C. for 2-3 h, then quenched under ice-cooling with 40 g ethanol, then with 2M HCl. The organic phase is separated and the aqueous phase extracted with t-butyl methyl ether. The combined organic layers are washed with conc. NaCl, then with water until pH=7. The organic phase is dried over MgSO$_4$, filtered and concentrated under reduced pressure. The residue is distilled over a short Vigreux column (124° C./0.1 Torr) to give 16 g (80%) of β-Georgywood as a colorless liquid (GC purity~90%).

Analytical Data:
IR (film): 2930 m, 1700 s (C=O), 1560 m, 1377 m, 1357 m, 1240 w, 1220 w, 1090 m.
GC/MS: 234 (25%, [M]$^+$), 219 (15%, [M-CH$_3$]$^+$), 191 (100%, [M-Ac]$^+$, 161 (20%), 135 (65%), 121 (40%), 105 (40%), 91 (30%), 69 (30%), 43 (55%).
$^1$H-NMR (CDCl$_3$, 400 MHz): 0.85 (d, 3H, J=6.9 Hz, Cl-Me), 0.99 (s, 3H), 1.02 (s, 3H), 1.06 (s, 3H), 1.4-2.2 (10 H, 5 CH$_2$), 2.15 (s, 3H, Ac-Me), 2.36 (q, 1H, J=6.9 Hz, Cl-H) ppm.
$^{13}$C-NMR (CDCl$_3$, 400 MHz): 19.1 (CH$_2$), 19.7 (CH$_3$), 21.0 (CH$_3$), 22.5 (CH$_2$), 24.9 (CH$_3$), 27.7 (CH$_2$), 28.9 (CH$_3$), 29.4 (CH$_3$), 30.8 (CH$_2$), 34.0 (C), 35.4 (CH), 40.1 (CH$_2$), 50.7 (C), 125.9 (C=), 136.9 (C=), 214.5 (C=O) ppm.

EXAMPLE 3

Cyclization of Pseudo-Georgywood With Crude MADC via MASI Activation of Aluminium in the Presence of AlCl$_3$: β-Georgywood 1.5 ml (ca. 0.013 mol) of the aluminium/methyl iodide/MASI mixture prepared according to example 1 is sprinkled via syringe onto a stirred mixture of 42.9 g (1.59 mol) of aluminium gritty (Fluka™ 11008) and 105.0 g (0.79 mol) of aluminium trichloride flakes (Fluka 06220) under 1 atm of methyl chloride at room temperature. The reaction starts almost at once and the initially solid reaction mixture progressively turns into a liquid. The methyl chloride absorption rate is kept approximately constant by gradually increasing the temperature from 25 to 120° C. over the next 2 h. The reaction is then allowed to proceed at 120° C. until no more gas absorption is observed (about 1 h). This happens after about 156.0 g (3.09 mol) of methyl chloride has been consumed. The crude molten MADC is cooled down to 70° C., the methyl chloride atmosphere is exchanged for an argon one and 810 g of dry toluene is added.

The ca. 25 wt % suspension of crude MADC in toluene thus obtained is cooled to 10-15° C. and 275.0 g (1.06 mol) of 90% pure pseudo-Georgywood is added dropwise. The mixture is heated at 70° C. until nearly complete cyclization of pseudo-Georgywood is detected by GC (about 2-3 h). The reaction mixture is cooled to 0° C. and pumped via a double-tipped needle on to 1.8 kg of ice-cooled 5% aqueous hydrochloric acid. The organic layer is separated, washed until neutral and refluxed for 2 h over 30.0 g of Montmorillonite K10, an acidic clay. Filtration and concentration of the organic layer under reduced pressure gives crude β-Georgywood, which is rectified over 3 weight % of Montmorillonite K10 through a 2.5×20 cm Vigreux column (105-110° C./1 mbar) to give 227 g (82.5% based on pseudo-Georgywood) β-Georgywood (GC-purity 86%) of a yellow colour.

Two further distillations over 10 weight % of paraffin oil and 3 weight % of Montmorillonite K10 give nearly colorless β-Georgywood.

Analytical data: Identical with those from Example 2

EXAMPLE 4

Cyclization of Pseudo-Georgywood With Crude MADC via EASB Activation of Aluminium in the Presence of AlCl$_3$: β-Georgywood 10.0 g (0.37 mol) of aluminium gritty (Fluka™ 11008) suspended in 87.7 g (0.81 mol) of ethyl bromide is refluxed for 18 hours at 40°-65° C. under nitrogen atmosphere. The crude EASB reaction mixture thus obtained can be stored under nitrogen atmosphere for several weeks without any loss of activity.

A stirred mixture containing 47.1 g (1.75 mol) of aluminium gritty (Fluka 11008) and 115.5 g (0.87 mol) of aluminium trichloride flakes (Fluka 06220) is heated for 30 minutes at 40-45° C. under 1 atm of methyl chloride. At this temperature, 9 ml (ca. 0.05 mol) of the above-prepared crude aluminium/ethyl bromide/EASB mixture is sprinkled via syringe on to the contents of the vessel and the reaction starts almost at once. The methyl chloride absorption rate is kept approximately constant by gradually increasing the temperature from 45 to 120° C. over the next 3 h and the initially solid reaction mixture progressively turns into a liquid. The reaction mixture is then heated for a further 3 h at 120° C., during which period of time gas absorption stops after an average amount of 186.0 g (3.69 mol) of methyl chloride has been consumed. The crude molten MADC is cooled to 70° C., the methyl chloride atmosphere is exchanged for an argon one and 810 g of dry toluene is added.

The ca. 27 wt % suspension of crude MADC in toluene thus obtained is cooled to 10-15° C. and 275.0 g (1.06 mol) of 90% pure pseudo-Georgywood is added dropwise. The mixture is heated to 70° C. until nearly complete cyclization of pseudo-Georgywood is detected by GC (about 4 h). The reaction mixture is cooled to 0° C. and pumped via a double-tipped needle on to 1.8 kg of ice-cooled 5% aqueous hydrochloric acid. The organic layer is separated, washed until neutral and concentrated under reduced pressure to give crude β-Georgywood which is rectified through a 2.5×31 cm Sulzer DX type column (105-110° C./1 mbar) to give 224.5 g (82%) β-Georgywood (GC purity 89%).

Analytical data: Identical with those from Example 2.

The invention claimed is:

1. A process for the preparation of methylaluminium dichloride comprising the steps of:

(i) reacting, by heating a material of the formula

R$_3$Al$_2$X$_3$, where R is C$_1$-C$_4$ alkyl and X is selected from bromine and iodine with an aluminium-containing material selected from metallic aluminium and a mixture of metallic aluminium and aluminium trichloride in an atmosphere of methyl chloride, with the proviso that when R is methyl and X is iodine, the aluminium-containing material is a mixture of aluminium and aluminium trichloride; and (ii) when the aluminium-containing material is metallic aluminium, adding aluminium trichloride to this reaction mixture and heating, to give a crude reaction product; and (iii) optionally obtaining methylaluminium dichloride from this crude reaction product.

2. A process according to claim 1, in which the material of the formula R$_3$Al$_2$X$_3$ is selected from methylaluminium sesquiiodide and ethylaluminium sesquibromide.

3. A process according to claim 1, in which the metallic aluminium is particulate metallic aluminium.

4. A process for preparing a compound of the Formula I

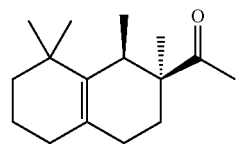

I comprising the addition of a compound of Formula II

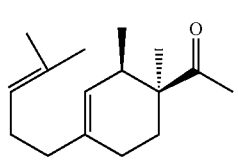

II to the crude reaction product of a reaction according to claim 1.

5. A process for the preparation of a compound of Formula I

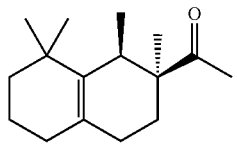

by cyclisation of a compound of Formula II

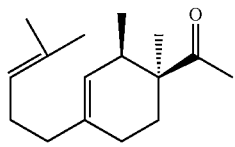

of a reaction mixture according to the steps of:
(i) reacting by heating a material of the formula
$R_3Al_2X_3$, where R is $C_1$-$C_4$ alkyl and X is selected from bromine and iodine with an aluminium-containing material selected from metallic aluminium and a mixture of metallic aluminium and aluminium trichloride in an atmosphere of methyl chloride, with the proviso that when R is methyl and X is iodine, the aluminium-containing material is a mixture of aluminium and aluminium trichloride; and (ii) when the aluminium-containing material is metallic aluminium, adding aluminium trichloride to this reaction mixture and heating; and (iii) adding to the mixture a compound of Formula (II) and heating to effect cyclisation of the compound of Formula (II).

6. The process according to claim 5 wherein the mixture containing the compound of Formula (II) are heated to 60°-70° C.

7. The process according to claim 5 wherein the mixture containing the compound of Formula (II) are heated for about 4 hours.

* * * * *